(12) United States Patent  (10) Patent No.: US 8,486,654 B2
Koo et al.  (45) Date of Patent: Jul. 16, 2013

(54) COMPOSITIONS AND METHODS FOR MEASURING 3,6-L-AHG TRANSFERASE ACTIVITY AND 3,6-L-AHG

(75) Inventors: Hyun Min Koo, Seoul (KR); Sung Min Park, Yongin-si (KR); Jae Chan Park, Yongin-si (KR); Kyoung Heon Kim, Seongnam-si (KR); In Geol Choi, Seoul (KR)

(73) Assignees: Samsung Electronics Co., Ltd., Suwon-si, Gyeonggi-do (KR); Korea University Research and Business Foundation, Seoul (KR)

( * ) Notice: Subject to any disclaimer, the term of this patent is extended or adjusted under 35 U.S.C. 154(b) by 0 days.

(21) Appl. No.: 13/034,387

(22) Filed: Feb. 24, 2011

(65) Prior Publication Data

US 2011/0306059 A1 Dec. 15, 2011

(30) Foreign Application Priority Data

Jun. 15, 2010 (KR) ........................ 10-2010-0056459

(51) Int. Cl.
G01N 33/573 (2006.01)
(52) U.S. Cl.
USPC .......................................................... 435/26
(58) Field of Classification Search
None
See application file for complete search history.

(56) References Cited

U.S. PATENT DOCUMENTS 5,260,197 A * 11/1993 Horiuchi et al. ................ 435/26

FOREIGN PATENT DOCUMENTS

KR  1020090112382 A  10/2009

OTHER PUBLICATIONS

Shin et al., Global metabolite profiling of agarose degradation by *Saccharophagus degradans* 2-40, 2010, New Biotechnology, 27(2): 156-168.*
Shin et al., Global metabolite profiling of agarose degradation by *Saccharophagus degradans* 2-40, 2010, New Biotechnol. 27(2):156-68.*
Ekborg, N. A., et al., *Saccharophagus degradans* gen. nov., sp. nov., a versatile marine degrader of complex polysaccharides, Int J Syst Evol Microbiol, 2005; 55:1545-1549.
Ekborg, N. A., et al., Genomic and Proteomic Analyses of the Agarolytic System Expressed by *Saccharophagus degradans* 2-40, Appl Environ Microbiol. 2006; 72(5): 3396-3405.
Kim, H.T. et al., Overexpression and molecular characterization of Aga50D from *Saccharophagus degradans* 2-40: an exo-type beta-agarase producing neoagarobiose, Appl Microbiol Biotechnol. 2010; 86: 227-234.

* cited by examiner

*Primary Examiner* — Jon P Weber
*Assistant Examiner* — Robert Yamasaki
(74) *Attorney, Agent, or Firm* — Leydig, Voit & Mayer, Ltd.

(57) ABSTRACT

Provided herein are a composition for measuring 3,6-anhydro-L-galactose (3,6-L-AHG) transferase activity by reduction of NADP to NADPH, and a method of measuring 3,6-L-AHG transferase activity using the same. The composition and method are useful for determining 3,6-L-AHG in a material containing 3,6-L-AHG such as algae biomass and industrial applications.

2 Claims, 3 Drawing Sheets

COMPOSITIONS AND METHODS FOR MEASURING 3,6-L-AHG TRANSFERASE ACTIVITY AND 3,6-L-AHG

CROSS-REFERENCE TO RELATED APPLICATION

This application claims priority to Korean Patent Application No. 10-2010-0056459, filed on Jun. 15, 2010, and all the benefits accruing therefrom under 35 U.S.C. §119, the content of which in its entirety is herein incorporated by reference.

BACKGROUND

1) Field

This disclosure relates to a composition for measuring 3,6-anhydro-L-galactose (3,6-L-AHG) transferase activity, a method for measuring 3,6-L-AHG transferase activity and a composition and method for quantitative analysis of 3,6-L-AHG.

2) Description of the Related Art

With globally increasing concern about exhaustion of resources and pollution of the environment by overuse of fossil fuels, new and renewable substitute energy resources for stably and continuously producing energy are being considered. In the ongoing development of such substitute energy resources, a technique of producing alcohol from biomass is receiving considerable attention.

Today, first generation alcohols using saccharides such as sugar cane or starches such as corn are being produced. However, these saccharides face the problems of competition as food and livestock feed, and saturation of agricultural land. For these reasons, second generation alcohols using lignocellulose, which comes from wood, the most abundant, rich and renewable resource in the world, are being developed.

In recent times, development of alcohol production using algae is ongoing. Since algae have the advantages of rapid growth, ease of mass-culturing, and a high uptake level of carbon dioxide, algae are considered to be an appropriate and new energy source. Due to a lower density than lignin, algae are more easily saccharified than biomass used for first and second generation alcohols, and also can achieve large scale production. In addition, as relatively abundant marine resources can be utilized, there is great potential.

One of the algae, red algae biomass, is usually composed of agar. Agar is a polysaccharide, including repeating sets of D-galactose and 3,6-L-AHG bound by 1,3- or 1,4-linkages. Among these, 3,6-L-AHG is a rare sugar, not commonly used in fermentation processes, and its applications are thus limited.

SUMMARY

To effectively use one of the main components of agar, 3,6-L-AHG, a method of measuring the activity of 3,6-L-AHG transferase, which mediates the conversion of 3,6-L-AHG and of quantitatively analyzing 3,6-L-AHG has to be developed. In addition, a method of distinguishing L-type 3,6-L-AHG from D-type is needed.

For this reason, exemplary embodiments provide a composition for measuring 3,6-L-AHG transferase activity and a method of measuring the activity using the composition.

In one aspect, a composition for measuring 3,6-L-AHG transferase activity is provided, the composition including nicotinamide adenine dinucleotide phosphate (NADP$^+$) as a coenzyme, 3,6-L-AHG as a substrate and a buffer. Here, the activity of the L-AHG transferase may be measured with the composition through reduction of NADP$^+$ to NADPH.

In another aspect, a method of measuring 3,6-L-AHG transferase activity using the above-mentioned composition is provided.

In an embodiment, the method includes contacting a certain enzyme extract with the composition, and measuring the amount of NADPH produced.

The reduction to NADPH may be determined by measuring absorbance at a wavelength of about 339 to 340 nm.

In still another aspect, a composition for quantitative analysis of 3,6-L-AHG is provided, the composition including an active fraction containing 3,6-L-AHG transferase, NADP$^+$ and a buffer.

When the composition for quantitative analysis reacts with a certain sample, the content of 3,6-L-AHG in the sample may be directly proportional to the content of NADPH. The content of the NADPH may be determined by measuring absorbance at about 339-340 nm.

In an embodiment, the active fraction containing 3,6-L-AHG transferase may be derived from *Saccharophagus degradans*.

In an embodiment, such an active fraction may be obtained by a method of purifying 3,6-anhydro-L-galactose (3,6-L-AHG) transferase from *Saccharophagus degradans*, comprising obtaining a crude extract of *Saccharophagus degradans*, adding ammonium sulfate $(((NH_4)_2SO_4)$ to the crude extract at a saturation level of 0 to 50% to induce precipitation, adding ammonium sulfate $(((NH_4)_2SO_4)$ to the resultant supernatant from the induced precipitation at a saturation level of 50 to 70% to induce a second precipitation, and fractionating the resultant precipitant from the second precipitation through anion-exchange chromatography to obtain 3,6-anhydro-L-galactose (3,6-L-AHG) transferase. The final purified 3,6-anhydro-L-galactose (3,6-L-AHG) transferase has an activity of about 2.5 to 3.0 U/mg.

BRIEF DESCRIPTION OF THE DRAWINGS

The above and other aspects of this disclosure will become more readily apparent by describing in further detail non-limiting example embodiments thereof with reference to the accompanying drawings, in which.

DETAILED DESCRIPTION

Figure 1:
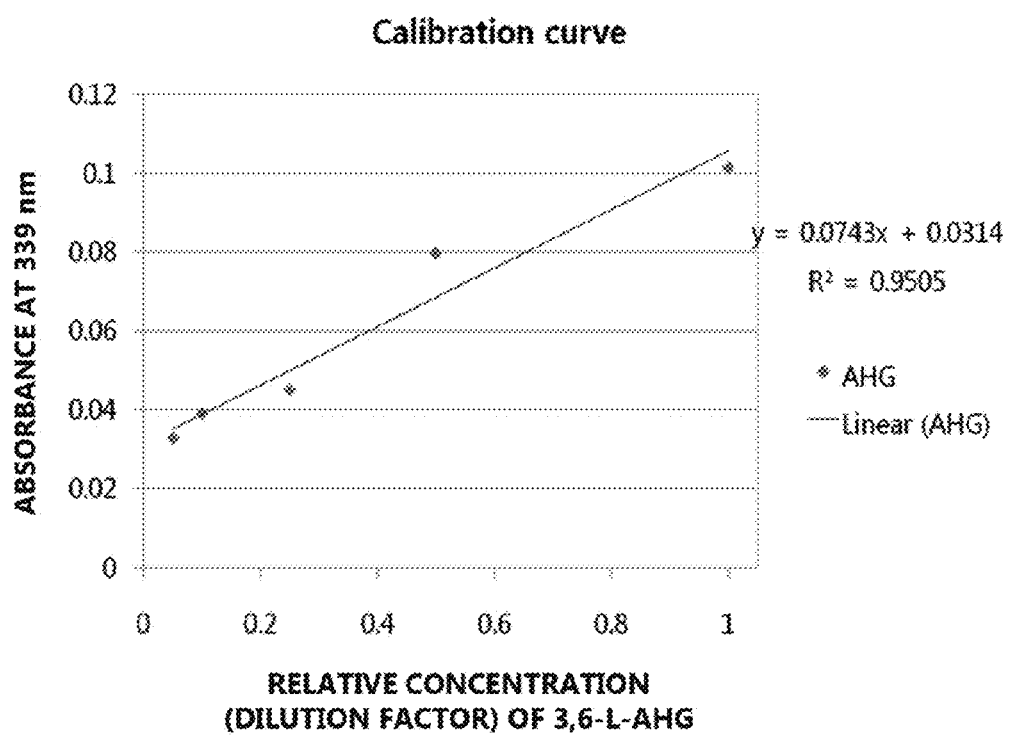
FIG. 1 is a graph showing a calibration curve for the content of 3,6-L-AHG (x axis) versus the content of NADPH (y axis) [x axis: relative concentration (dilution factor) of 3,6-L-AHG, y axis: absorbance at 339 nm]

The invention now will be described more fully hereinafter with reference to the accompanying drawings, in which various non-limiting example embodiments are shown. This invention may, however, be embodied in many different forms, and should not be construed as limited to the example embodiments set forth herein. Rather, these example embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated regions, integers, steps, operations, elements, and/or components, but do not preclude the presence or addition of one or more other regions, integers, steps, operations, elements, components, and/or groups thereof. The modifier "about" used in connection with a quantity is inclusive of the stated value and has the meaning dictated by the context (e.g., includes the degree of error associated with measurement of the particular quantity).

Furthermore, relative terms, such as "lower" or "bottom" and "upper" or "top," may be used herein to describe one element's relationship to another element as illustrated in the figures. It will be understood that relative terms are intended to encompass different orientations of the device in addition to the orientation depicted in the figures. For example, if the device in one of the figures is turned over, elements described as being on the "lower" side of other elements would then be oriented on "upper" sides of the other elements. The term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

One or more embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear portions. Moreover, sharp angles that are illustrated may be rounded. Thus, the regions illustrated in the figures are schematic in nature and their shapes are not intended to illustrate the precise shape of a region and are not intended to limit the scope of the claims.

The term "enzyme activity" generally refers to a catalytic ability of an enzyme in a reaction mechanism, and the term "transferase activity" used herein can be determined by reduction of $NADP^+$ as a coenzyme to NADPH.

The term "coenzyme" refers to a non-protein element binding to an apoenzyme, which is a factor assisting an enzyme reaction by changing a chemical structure during an enzyme reaction and delivering functional elements such as atoms or electrons to a reaction substrate. The coenzyme may be referred to as a "cofactor" or "helper enzyme." Examples of coenzymes include nicotinamide adenine dinucleotide (NAD), NADH, nicotinamide adenine dinucleotide phosphate (NADP), NADPH, adenosine triphosphate (ATP), phosphoadenylyl sulfate (PAPS), uridine diphosphate (UDP), cytidine diphosphate (CDP), guanosine triphosphate (GTP), inosine triphosphate (ITP), and Coenzyme A (CoA). However, the composition for measuring L-AHG transferase activity and the composition for quantitative analysis of L-AHG described herein include NADP as an effective coenzyme.

The term "substrate" refers to a material affected by enzyme action, and includes a compound whose chemical structure is changed due to the enzyme action.

Composition for Measuring 3,6-L-AHG Activity

According to an aspect of the present disclosure, a composition for measuring 3,6-L-AHG transferase activity is provided.

The composition includes $NADP^+$ as a coenzyme, 3,6-L-AHG as a substrate and a buffer. In the case of an enzyme extract having an activity of L-AHG transferase, as the coenzyme $NADP^+$ is converted into NADPH, conversion of the reaction substrate, L-AHG, is mediated. Thus, the activity of the L-AHG transferase may be measured by reduction of $NADP^+$ to NADPH.

Here, a certain enzyme extract means an enzyme extract to be subjected to measurement of activity of 3,6-L-AHG transferase.

The substrate, 3,6-L-AHG, is a component of agar present in various red algae such as *Gelidium amansii*, and may be obtained from red algae, but the present disclosure is not limited thereto. The buffer serves to maintain optimum conditions in which the enzyme activity is at the highest level, as well as maintaining irreversible reduction of $NADP^+$ to NADPH. Tris-HCl (pH 8.0) is an example of the buffer.

With the composition for measuring activity, the activity of 3,6-L-AHG transferase may be effectively measured. Thus, the composition for activity measurement may be used to measure whether a certain enzyme extract has an activity of L-AHG transferase. For example, the composition for activity measurement may be added to an enzyme extract, and the activity can be measured by determining whether reduction of $NADP^+$ to NADPH occurs.

The method of observing $NADP^+$ reduction to NADPH is not particularly limited. Any method known in the art can be used. For example, the reduction may be detected by a spectroscopic method, for example, by measuring absorbance at a wavelength of about 339 to 340 nm. In this case, the composition should not include other components, for example another coenzyme (e.g., NADH), having significant absorbance at about 339 to 340 nm, other than $NADP^+$.

Method of Measuring 3,6-L-AHG Transferase Activity

According to another aspect of the present disclosure, a method of measuring 3,6-L-AHG transferase activity using a composition for measuring 3,6-L-AHG transferase activity is provided.

In one embodiment, the method includes contacting a test enzyme extract with the composition for measuring 3,6-L-AHG transferase activity described above and detecting reduction to NADPH.

The reduction to NADPH may be detected by measuring absorbance at about 339 to 340 nm. Here, the reduction to NADPH indicates that 3,6-L-AHG is converted, and thus it can be determined whether the test enzyme extract has the 3,6-L-AHG transferase activity based on the amount of NADPH formed.

When the amount of NADPH formed per unit time is measured, the enzyme activity may be measured in a reaction rate.

Composition for Quantitative Analysis of 3,6-L-AHG

It is currently known that thin film chromatography and spectrometry are used for qualitative analysis for 3,6-L-AHG and other liquid chromatography methods are used for quantitative analysis for 3,6-L-AHG. However, there is no standardized method, and the above methods cannot distinguish 3,6-L-AHG from the enantiomer, D-AHG.

Therefore, a method and composition for quantitative analysis of 3,6-L-AHG are provided herein. The method can distinguish 3,6-L-AHG from its D-form enantiomer based on the substrate preferences of 3,6-L-AHG transferase.

In one example, the composition for quantitative analysis includes an active fraction containing 3,6-L-AHG transferase, $NADP^+$, and a buffer.

When 3,6-L-AHG is present in a certain sample, 3,6-L-AHG is converted by the 3,6-L-AHG transferase, resulting in reduction of $NADP^+$ to NADPH. Here, a change in content of 3,6-L-AHG in the sample is directly proportional to a change in content of NADP. In other words, one molecule of 3,6-L-AHG is converted, while one molecule of $NADP^+$ is converted into NADPH.

Here, the certain sample refers to a sample to be subjected to detection of the presence and/or quantitative amount of 3,6-L-AHG in the sample.

Thus, for quantitative analysis of 3,6-L-AHG in a sample, the composition for quantitative analysis according to the present disclosure is added to the sample under conditions that permit the 3,6-L-AHG transferase to catalyze the reaction of 3,6-L-AHG present in the sample, and the amount of NADPH formed is measured. The amount of NADPH can be determined by measuring absorbance at about 339 to 340 nm.

FIG. 1 is a calibration curve for content of 3,6-L-AHG (x axis) versus content of NADPH (y axis) determined in various calibration samples. Here, the absorbance (y axis) at 339 nm indicates the content of NADPH in a sample. Accordingly, the content of 3,6-L-AHG in a test sample may be determined from the absorbance (y axis) at 339 nm of the test sample by comparison with the calibration curve of FIG. 1. For example, when the composition for quantitative analysis reacts with a certain sample, NADPH is produced in proportion to the change in content of 3,6-L-AHG in the sample produced by the 3.6-L-AHG transferase reaction. As a result, the content of NADPH may be obtained by measuring absorbance at 339 nm. The content of 3,6-L-AHG on the x axis can be estimated by substituting the measured absorbance value (y-coordinate) into the regression equation determined for the calibration curve of FIG. 1.

The active fraction containing the 3,6-L-AHG transferase, although not particularly limited, may be obtained from various strains which use 3,6-L-AHG in their metabolism. For example, it was found by the present inventors that 3,6-L-AHG transferase is present in an active fraction obtained from *Saccharophagus degradans*.

The term "purified" with respect to an enzyme, e.g., 3,6-L-AHG transferase, refers to a change from a natural state, that is, changed and/or removed from its original environment by human means. For example, an enzyme naturally present in an organism is not "purified," but the same enzyme when separated from a natural co-existing substance by the action of a human is "purified."

A method of obtaining the purified active fraction of *Saccharophagus degradans* is not particularly limited, but may use an enzyme fractionation technique known in the art. Examples of enzyme fractionation techniques include coarse fractionation techniques such as ammonium sulfate fractionation (salting out), organic solvent precipitation, pH treatment, and membrane fractionation; chromatography techniques such as affinity chromatography, ion-exchange chromatography, and gel or filter chromatography; and electrophoresis techniques such as SDS-PAGE, isoelectric focusing, and 2-D fluorescence difference gel electrophoresis. These fractionation techniques may be employed in combination.

Figure 2:
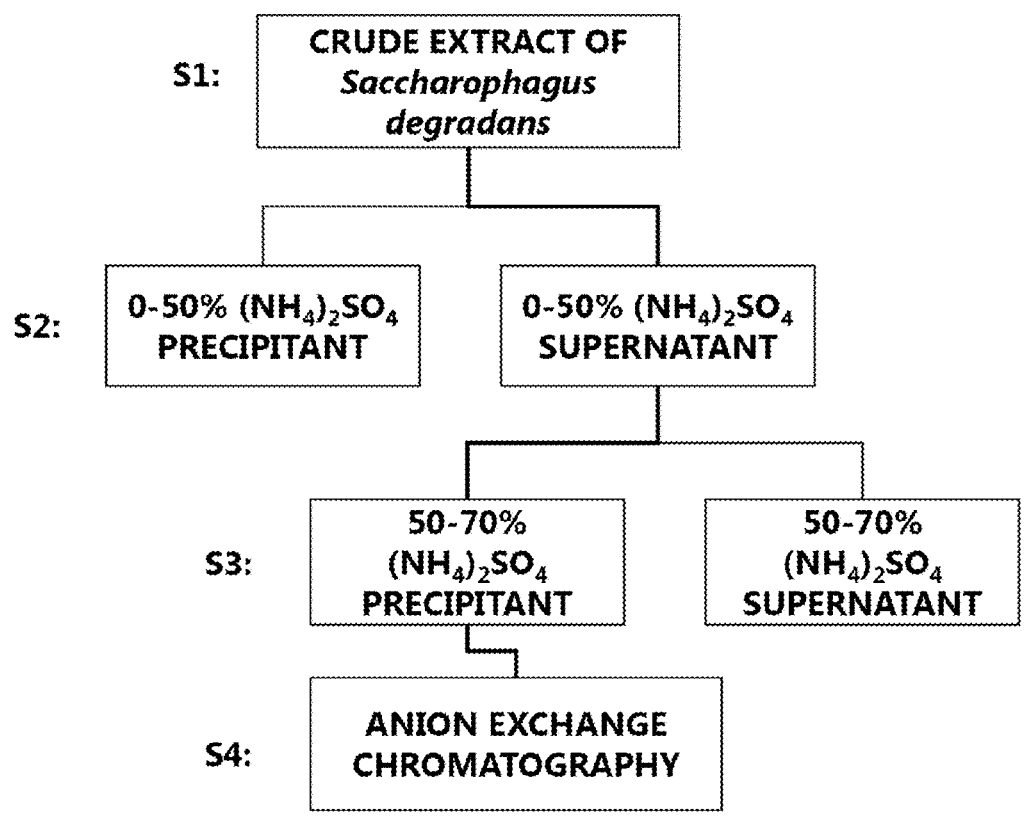
FIG. 2 is a schematic diagram showing a process of obtaining purified 3,6-L-AHG transferase from *Saccharophagus degradans*.

FIG. 2 illustrates a method of obtaining an active fraction containing 3,6-L-AHG transferase from *Saccharophagus degradans*. Referring to FIG. 2, the active fraction may be obtained by: obtaining a crude extract of *Saccharophagus degradans* (S1); adding ammonium sulfate (($NH_4)_2SO_4$) to the crude extract at a saturation level of 0 to 50% to induce precipitation (S2); adding ammonium sulfate (($NH_4)_2SO_4$) to the resultant supernatant at a saturation level of 50 to 70% to induce precipitation (S3); and performing fractionation on the resultant precipitant from the precipitation by anion-exchange chromatography (S4).

The resulting active fraction may have a specific 3,6-L-AHG transferase activity of about 2.5 to 3.0. The specific 3,6-L-AHG transferase activity is expressed as unit number per milligram of total protein. The 3,6-L-AHG transferase activity is determined by the methods described above and unit number (U) represents the amount of catalyzed reduction of 1 nM $NADP^+$ per minute measured under the test conditions.

The present disclosure will now be described with reference to the following Preparation Examples and Experimental Examples.

Preparation Example 1

Crude Extract of *Saccharophagus degradans*

10 ml of *Saccharophagus degradans* 2-40 (hereinafter, "sde") cultured from a single colony is incubated in 1 L of minimal medium containing 0.2% agar at 30° C. for 24 hours, and centrifuged at 4000 rpm for 30 minutes, thereby obtaining 5 g of probiotics.

The probiotics are disrupted using a sonifier 450 (Branson, USA), centrifuged at 15000 rpm at 4° C. for 1 hour, and filtered through a 0.45-μm filter paper (Sartorius stedim biotech, Germany), thereby obtaining a crude extract.

Preparation Example 2

Purification of sde Crude Extract

Active fractionation is performed on the crude extract obtained in Preparation Example 1 by ammonium sulfate ((NH$_4$)$_2$SO$_4$) fractionation at a saturation level of 0 to 50% (NH$_4$)$_2$SO$_4$. Then, the supernatant obtained from this precipitation is treated with ammonium sulfate ((NH$_4$)$_2$SO$_4$) at a saturation level of 50 to 70%. The precipitant obtained at 50 to 70% (NH$_4$)$_2$SO$_4$ is solubilized in a loading buffer (20 Mm Tris HCl, pH 8.0) and subjected to anion exchange chromatography using a HiTrap™ Q column (GE healthcare, USA), and the solublized precipitant is eluted with 0-1M NaCl gradient and obtained a final active enzyme fraction at 150~350 mM NaCl. The activities of the final fractionated protein is summarized in Table 1:

TABLE 1

Purification Data from sde Crude Extract

| Active Fraction | Total Activity* (U) | Total Protein (mg) | Specific Activity** (U/mg) | Protein Yield (%) |
|---|---|---|---|---|
| Crude Extract | 455.4 | 635 | 0.72 | 100 |
| 50-70% (NH$_4$)$_2$SO$_4$ | 75.4 | 35.33 | 2.13 | 16.56 |
| Anion Exchange | 26.7 | 9.36 | 2.85 | 5.86 |

*Unit number (U) represents an amount of catalyzing reduction of 1 nM NADP$^+$ per minute under test conditions.
**Specific activity represents a unit number (U) per milligram of total protein.

Preparation Example 3

Preparation of Composition for Measuring 3,6-L-AHG Transferase Activity 5 mM of NADP$^+$, 20 μg of 3,6-L-AHG and 20 mM of Tris-HCl (pH 8.0) buffer are mixed to prepare 100 μl of composition for measuring activity.

Experimental Example 1

Measurement of Enzyme Activity for Each Purification Step of sde Crude Extract

Activities of 3,6-L-AHG transferase are measured for each purification step of the sde Crude Extract. 10 μl of the crude extract obtained in Preparation Example 1, 10 μl of the active fraction from the 50 to 70% (NH$_4$)$_2$SO$_4$ precipitation according to Preparation Example 2, or 10 μl of the active fraction obtained by anion exchange chromatography is added to a 100 μl composition for measuring activity as prepared in Preparation Example 3. Then, the absorbance at 339 nm is measured as a function of time using a microplate spectrophotometer (Bio-Tek Instruments, Inc.) according to an End-point UV method to measure the content of NADPH. The results are shown in FIG. 3.

Figure 3:
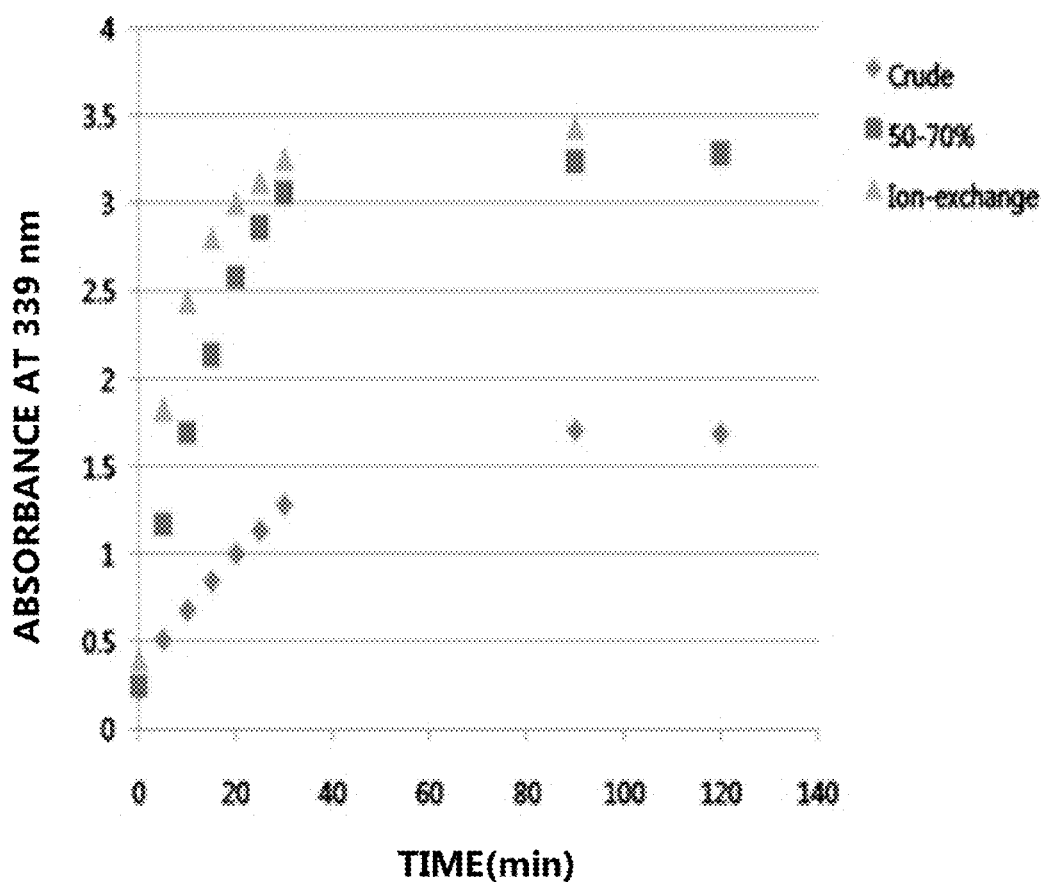
FIG. 3 is a graph of enzyme activity measured at each step of purification of 3,6-L-AHG transferase from *Saccharophagus degradans* of Experimental Example 1 [x axis: time (min), y axis: absorbance at 339 nm].

Referring to FIG. 3, it can be seen that absorbance at 339 nm increases over the 140 minute reaction time for each of the enzyme fractions, indicating reduction to NADPH occurred in each of the three enzyme fraction samples.

Comparative Example 1

NAD$^+$, NADH, and NADPH are each used as a coenzyme in the composition for measuring 3,6-L-AHG Transferase Activity, instead of NADP$^+$ used in the composition of Preparation Example 3. 10 μl of the final active fraction obtained in Preparation Example 2 is added to each of the comparative compositions for measuring activity to prepare a sample composition. Then, to detect coenzyme usage, the absorbance is measured at 339 nm. The results are summarized in Table 2.

Referring to Table 2, it can be seen that when using coenzymes other than NADP$^+$, no activity of 3,6-L-AHG transferase is detected.

TABLE 2

Effect of Coenzyme on Enzyme Activity Determined by Absorbance ($\Delta A_{339}$)

| Coenzymes added | Activity |
|---|---|
| NAD$^+$ | n.d.* |
| NADP$^+$ | +++ |
| NADH | n.d. |
| NADPH | n.d. |

*n.d.: not detected

Preparation Example 4

Composition for Quantitative Analysis of 3,6-L-AHG 7.5 μl of the final active fraction obtained in Preparation Example 2, 0.1 mM of NADP$^+$, and 50 mM of Tris-HCl (pH 8.0) are mixed to prepare 100 μl of a composition for quantitative analysis of 3,6-L-AHG.

Experimental Example 2

An amount of 3,6-L-AHG is added to various 100 μl samples of the composition for quantitative analysis of 3,6-L-AHG obtained in Preparation Example 4 to achieve dilution factors for the 3,6-L-AHG of 1, 0.5, 0.25, 0.1 and 0.05 in terms of relative concentrations. A relative 3,6-L-AHG concentration of 1 corresponds to 20 mg/mL. Reaction is carried out for 50 minutes, and then absorbance is measured at 339 nm using a microplate spectrophotometer (Bio-Tek Instruments, Inc.) according to the End-point UV method. The results are shown in FIG. 1. FIG. 1 shows that in a 50 minute reaction, the amount of NADPH produced is linearly related to the amount of 3,6-L-AHG in the sample.

The invention should not be construed as being limited to the embodiments set forth herein. Rather, these embodiments are provided so that this disclosure will be thorough and complete and will fully convey the concept of the present invention to those of ordinary skill in the art.

While the invention has been particularly shown and described with reference to embodiments thereof, it will be understood by those of ordinary skill in the art that various changes in form and details may be made therein without departing from the spirit or scope of the invention as defined by the following claims.

What is claimed is:

1. A method of measuring enzymatic modification of 3,6-anhydro-L-galactose (3,6-L-AHG), comprising:
    contacting an enzyme extract with a composition comprising NADP$^+$, 3,6-L-AHG, and a buffer; and
    measuring the amount of NADPH produced.
2. The method of claim 1, wherein amount of NADPH is determined by measuring absorbance at a wavelength of about 339 to 340 nm.

* * * * *